US00PP17445P2

(12) United States Plant Patent
de Bont

(10) Patent No.: US PP17,445 P2
(45) Date of Patent: Feb. 27, 2007

(54) ***COLEUS* PLANT NAMED 'SCOLK1'**

(50) Latin Name: *Coleus blumei*
Varietal Denomination: ScolK1

(75) Inventor: Diony de Bont, Alphen aan den Rijn (NL)

(73) Assignee: Paul Ecke Ranch, Encinitas, CA (US)

( * ) Notice: Subject to any disclaimer, the term of this patent is extended or adjusted under 35 U.S.C. 154(b) by 35 days.

(21) Appl. No.: 11/146,239

(22) Filed: Jun. 6, 2005

(51) Int. Cl.
*A01H 5/00* (2006.01)

(52) U.S. Cl. ..... Plt./373

(58) Field of Classification Search ..... Plt./373
See application file for complete search history.

*Primary Examiner*—Wendy Haas
(74) *Attorney, Agent, or Firm*—C. A. Whealy

(57) ABSTRACT

A new and distinct cultivar of *Coleus* plant named 'ScolK1', characterized by its compact, upright, outwardly spreading and mounded plant habit; freely branching growth habit; and light green-colored leaves with very dark purple-colored margins, veins and bases and light green-colored midveins and splashes.

1 Drawing Sheet

Botanical designation: *Coleus blumei.*
Cultivar denomination: 'ScolK1'.

BACKGROUND OF THE INVENTION

The present Invention relates to a new and distinct cultivar of *Coleus* plant, botanically known as *Coleus blumei,* and hereinafter referred to by the cultivar name ScolK1.

The new *Coleus* is a naturally-occurring whole plant mutation of a selection of the *Coleus blumei* 'Saber Mix', not patented. The new *Coleus* was discovered and selected by the Inventor as a plant within a population of plants of the parent selection in a controlled environment in Ter Aar, The Netherlands in 2001. The selection of the new *Coleus* was based on its unique leaf coloration.

Asexual reproduction of the new cultivar by terminal cuttings in Ter Aar, The Netherlands since 2001, has shown that the unique features of this new *Coleus* are stable and reproduced true to type in successive generations.

SUMMARY OF THE INVENTION

Plants of the cultivar ScolK1 have not been observed under all possible environmental conditions. The phenotype may vary somewhat with variations in environment such as temperature and light intensity without, however, any variance in genotype.

The following traits have been repeatedly observed and are determined to be the unique characteristics of 'ScolK1'. These characteristics in combination distinguish 'ScolK1' as a new and distinct cultivar:

1. Compact, upright, outwardly spreading and mounded plant habit.
2. Freely branching growth habit.
3. Light green-colored leaves with very dark purple-colored margins, veins and bases and light green-colored midveins and splashes.

Plants of the new *Coleus* differ primarily from plants of the parent selection in leaf coloration.

Plants of the new *Coleus* can be compared to plants of the cultivar Kiwi Fern, not patented. In side-by-side comparisons conducted in Ter Aar, The Netherlands, plants of the new *Coleus* differed from plants of the cultivar Kiwi Fern in the following characteristics:

1. Plants of the new *Coleus* and the cultivar Kiwi Fern differed in leaf shape.
2. Plants of the new *Coleus* and the cultivar Kiwi Fern differed in leaf coloration as plants of the cultivar Kiwi Fern had brown-colored leaves with yellow-colored margins.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Coleus.*

The photograph at the bottom of the sheet comprises a side perspective view of typical plant of 'ScolK1' grown in a container.

The photograph at the top of the sheet comprises a close-up view of typical leaves of 'ScolK1'.

DETAILED BOTANICAL DESCRIPTION

The cultivar ScolK1 has not been observed under all possible environmental conditions. The phenotype may vary somewhat with variations in environment such as temperature and light intensity without, however, any variance in genotype.

The aforementioned photographs, following observations and measurements describe plants grown during the summer and fall in Encinitas, Calif., in a polyethylene-covered greenhouse and under conditions which approximate commercial production cultural and environmental conditions. Plants were about six weeks from rooted cuttings and were grown in 13-cm containers. Plants were pinched one time. During the production of the plants, day temperatures averaged 27° C., night temperatures averaged 19° C. and light levels averaged about 4,000 footcandles.

In the following description, color references are made to The Royal Horticultural Society Colour Chart, 1995 Edition, except where general terms of ordinary dictionary significance are used.

Botanical classification: *Coleus blumei* cultivar ScolK1.

Parentage: Naturally-occurring whole plant mutation of a selection of the *Coleus blumei* 'Saber Mix', not patented.

Propagation:

*Type cutting.*—Terminal cuttings.

*Time to initiate roots.*—Summer: About 7 days at 20° C. Winter: About 9 days at 20° C.

*Time to develop roots.*—Summer: About 18 days at 20° C. Winter: About 20 days at 20° C.

*Root description.*—Fine; white in color.

*Rooting habit.*—Freely branching, dense.

Plant description:

*Form.*—Compact, upright, outwardly spreading and mounded plant habit. Vigorous growth habit; moderate to rapid growth rate.

*Plant height.*—About 21 cm.

*Plant diameter, single plant.*—About 40 cm.

*Branching habit.*—Freely branching with about nine lateral branches per plant.

*Lateral branches.*—Length: About 20 cm. Diameter: About 4 mm. Internode length: About 4 cm. Shape, in cross-section: Squarish. Texture: Pubescent. Color: 145C or 187A.

*Foliage description.*—Arrangement: Opposite; simple. Length: About 7.8 cm. Width: About 5.2 cm. Shape: Elliptic with deeply incised rounded serrations. Apex: Acute to acuminate. Base: Attenuate. Margin: Deeply incised rounded serrations. Texture, upper and lower surfaces: Smooth, glabrous. Venation pattern: Pinnate, arcuate. Color: Developing foliage, upper and lower surfaces: Darker than 187A with random central splashes of 146A. Fully expanded foliage, upper and lower surfaces: Ground color, 146A; towards the base and at margins and veins, darker than 187A; midveins and random small random splashes, 145A. Venation, upper and lower surfaces: Similar to lamina. Petiole length: About 1.8 cm. Petiole diameter: About 2.5 mm. Petiole texture, upper and lower surfaces: Pubescent. Petiole color, upper and lower surfaces: 187A.

Flower description: Flower development has not been observed.

Disease/pest resistance: Plants of the new *Coleus* have not been noted to be resistant to pathogens or pests common to *Coleus*.

Temperature tolerance: Plants of the new *Coleus* have been observed to tolerate temperatures from 4° C. to 32° C.

It is claimed:

1. A new and distinct cultivar of *Coleus* plant named 'ScolK1', as illustrated and described.

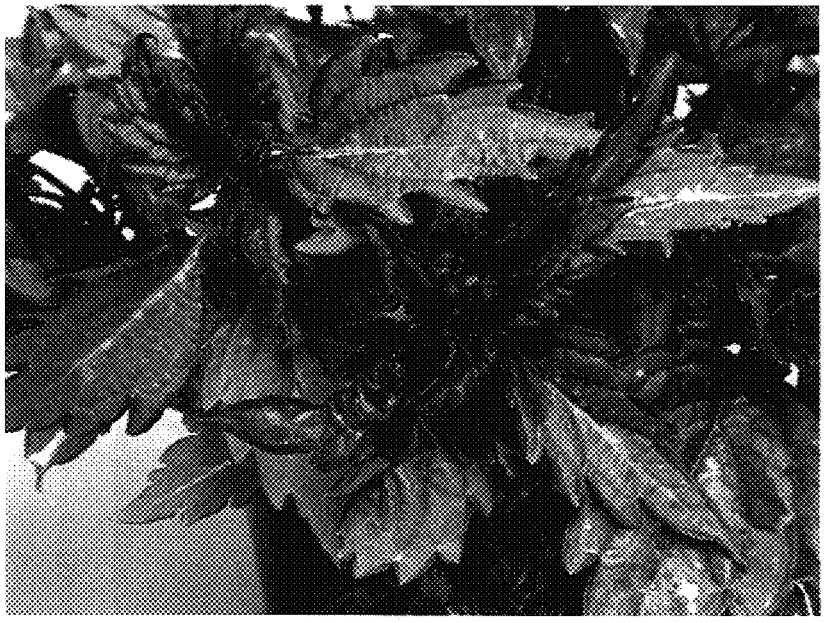
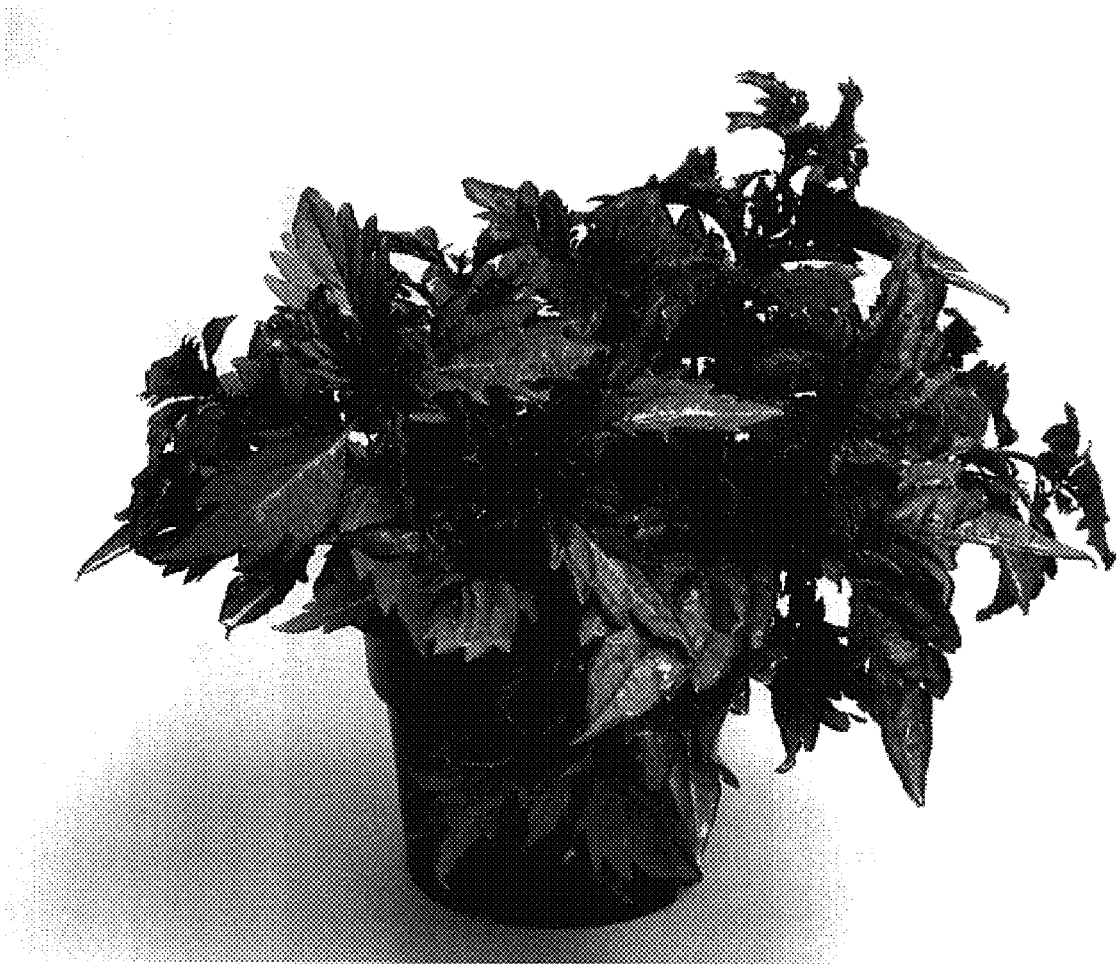

* * * * *